US009487781B2

(12) United States Patent
Yerushalmi

(10) Patent No.: US 9,487,781 B2
(45) Date of Patent: Nov. 8, 2016

(54) COMPOSITIONS AND METHODS FOR TREATMENT OF OVARIAN CANCER

(71) Applicant: Rosetta Genomics Ltd., Rehovot (IL)

(72) Inventor: Noga Yerushalmi, Nes-Ziona (IL)

(73) Assignee: Rosetta Genomics Ltd., Rehovot (IL)

( * ) Notice: Subject to any disclaimer, the term of this patent is extended or adjusted under 35 U.S.C. 154(b) by 0 days.

(21) Appl. No.: 14/505,548

(22) Filed: Oct. 3, 2014

(65) Prior Publication Data

US 2015/0031751 A1 Jan. 29, 2015

Related U.S. Application Data

(62) Division of application No. 13/977,787, filed as application No. PCT/IL2011/000892 on Nov. 20, 2011, now Pat. No. 8,883,757.

(60) Provisional application No. 61/429,194, filed on Jan. 3, 2011.

(51) Int. Cl.
*C12N 15/11* (2006.01)
*C12N 15/113* (2010.01)
*A61K 31/7088* (2006.01)
*A61K 45/06* (2006.01)

(52) U.S. Cl.
CPC ......... *C12N 15/113* (2013.01); *A61K 31/7088* (2013.01); *A61K 45/06* (2013.01); *C12N 2310/11* (2013.01); *C12N 2310/113* (2013.01); *C12N 2310/141* (2013.01); *C12N 2310/321* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 6,506,559 B1 | 1/2003 | Fire et al. | |
| 2005/0107326 A1 | 5/2005 | Norris et al. | |
| 2005/0182005 A1 | 8/2005 | Tuschl et al. | |
| 2005/0261218 A1* | 11/2005 | Esau | C12N 15/111 514/44 A |
| 2009/0192102 A1 | 7/2009 | Bader et al. | |
| 2009/0220589 A1 | 9/2009 | Trieu et al. | |
| 2010/0029003 A1 | 2/2010 | Bartel et al. | |
| 2010/0249213 A1 | 9/2010 | Croce | |

FOREIGN PATENT DOCUMENTS

| | | |
|---|---|---|
| WO | 9323569 | 11/1993 |
| WO | 9402595 | 2/1994 |
| WO | 9904819 | 2/1999 |
| WO | 9905094 | 2/1999 |

OTHER PUBLICATIONS

Zhu et al, Role of MicroRNA miR-27a and miR-451 in the regulation of MDR1/P-glycoprotein expression in human cancer cells, 2008, 76: 582-588.*
Yang et al, Lysophosphatidic Acid Activates Telomerase in Ovarian Cancer Cells Through Hypoxia-Inducible Factor-1a and the PI3K Pathway, 2008, Journal of Cellular Biochemistry, 105: 1194-1201.*
Stenvang et al, Inhibition of microRNA function by antimiR oligonucleotides, 2012, Silence, 3: 1-17.*
du Bois, A Randomized Clinical Trial of Cisplatin/Paclitaxel Versus Carboplatin/Paclitaxel as First-Line Treatment of Ovarian Cancer, 2003, Journal Natl Cancer Inst, v. 95, 17: 1320-1329.*
Li et al, MiR-27a modulates MDR1/P-glycoprotein expression by targeting HIPK2 in human ovarian cancer cells, published online Jul. 10, 2010, Gynecologic Oncology, 119: 125-130.*
International Search Report in PCT/IL2011/00892, mailed Apr. 8, 2012.
Nagaraja et al., "A Link between mir-100 and FRAP1/mTOR in Clear Cell Ovarian Cancer," Mol. Endocrinol. Feb. 2010, vol. 24(2), pp. 447-463.
Nam et al., "MicroRNA Expression Profiles in Serous Ovarian Carcinoma," Clin. Cancer Res., May 1, 2008, vol. 14, No. 9, pp. 2690-2695.
Wyman et al.,"Repertoire of microRNAs in Epithelial Ovarian Cancer as Determined by Next Generation Sequencing of Small RNA cDNA Libraries" PLoS One, Apr. 2009, vol. 4, Issue 4, e5311.
Giannakakis et al., "miR-210 links hypoxia with cell cycle regulation and is deleted in human epithelial ovarian cancer," 2008, Cancer Biology and Therapy, 7, 2: 255-264.
Akhtar et al., "Cellular uptake and intracellular fate of antisense oligonucleotides," Trends in Cell Biology, May 1992, pp. 139-144, vol. 2.
Bartel et al., "MicroRNAs: At the Root of Plant Development?" Plant Physiology, Jun. 2003, pp. 709-717, vol. 132.
Bartel D.P., "MicroRNAs: Genomics, Biogenesis, Mechanism, and Function," Cell, Jan. 2004, pp. 281-297, vol. 116.
Brennecke et al., "Principles of MicroRNA-Target Recognition," PLoS Biology, Mar. 2005, e85, pp. 0001-0015, vol. 3, No. 3.
Calin et al., "MicroRNA signatures in human cancers," Nature Reviews/Cancer, Nov. 2006, pp. 857-866, vol. 6.
Furth et al., "Gene Transfer into Somatic Tissues by Jet Injection," Analytical Biochemistry, 1992, pp. 365-368, vol. 205.
Doench et al., "Specificity of microRNA target selection in translational repression," Genes Dev., 2004, pp. 504-511, vol. 18.
Gold B.G., "Axonal Regeneration of Sensory Nerves is Delayed by Continuous Intrathecal Infusion of Nerve Growth Factor," Neuroscience, 1997, pp. 1153-1158, vol. 76, No. 4.
Hofacker et al., "Fast Folding and Comparison of RNA Secondary Structures," Monatshefte fur Chemie, 1994, pp. 167-188, vol. 125.
Jemal et al., "Cancer Statistics," CA Cancer J Clin, Jan./Feb. 2007, pp. 43-66, vol. 57, No. 1.
Krutzfeldt et al., "Silencing of microRNAs in vivo with 'antagomirs'," Nature, Letters 2005, pp. 1-5.

(Continued)

*Primary Examiner* — Tracy Vivlemore
*Assistant Examiner* — Kate Poliakova-Georgantas
(74) *Attorney, Agent, or Firm* — Polsinelli PC; Ron Galant

(57) ABSTRACT

The disclosure provides compositions and methods for treating an ovarian cancer in a subject. More specifically, the disclosure provides microRNA (miRNA) inhibitor molecules that target to different miRNAs for treating different types of ovarian cancers in a subject. Furthermore, different modifications of miRNA inhibitor molecules as well as different derivatives of miRNA inhibitor molecules are also described.

16 Claims, 5 Drawing Sheets

(56) References Cited

OTHER PUBLICATIONS

Lewis et al., "Conserved Seed Pairing, Often Flanked by Adenosines, Indicates that Thousands of Human Genes are MicroRNA Targets," Cell, Jan. 2005, pp. 15-20, vol. 120.

Nogrady et al., Medicinal Chemistry: A Molecular and Biochemical Approach, Third Ed., pp. 338-392, Oxford University Press.

Rossi J.J., "Receptor-targeted siRNAs," Nature Biotechnology, Jun. 2005, pp. 682-684, vol. 23, No. 6.

Song et al., "Antibody mediated in vivo delivery of small interfering RNAs via cell-surface receptors," Nature Biotechnology, Jun. 2005, pp. 709-717, vol. 23, No. 6.

Soutschek et al., "Therapeutic silencing of an endogenous gene by systemic administration of modified siRNAs," Nature, Nov. 2004, pp. 173-178, vol. 432.

Tang et al., "Genetic immunization is a simple method for eliciting an immune response," Nature, Mar. 1992, pp. 152-154, vol. 356.

Yi et al., "Morphogenesis in skin is governed by discrete sets of differentially expressed microRNAs," Nature Genetics, Advance Online Publication, 2006, pp. 1-7, Nature Publishing Group, http://www.nature.com/naturegenetics>.

\* cited by examiner

COMPOSITIONS AND METHODS FOR TREATMENT OF OVARIAN CANCER

CROSS REFERENCE TO RELATED APPLICATIONS

The present application claims priority under 35 U.S.C. §119(e) to U.S. Provisional Application No. 61/429,194 filed Jan. 3, 2011, which is herein incorporated by reference in its entirety.

FIELD OF THE INVENTION

The invention relates to compositions and methods for the treatment of ovarian cancer subjects. Specifically the invention relates to microRNA inhibitor molecules associated with the treatment of ovarian cancer subjects, as well as various nucleic acid molecules relating thereto or derived therefrom.

BACKGROUND OF THE INVENTION

Epithelial ovarian cancer (EOC) is the fifth leading cause of cancer-related deaths in women in the United States and the leading cause of gynecologic cancer related deaths (Jemal A, Siegel et. al, Cancer statistics, 2007, CA Cancer J Clin 2007; 57:43-66). Annually, there are more than 22,000 new cases of ovarian cancer in the United States and over 16,000 deaths. Despite efforts to develop an effective ovarian cancer screening method, most patients still present with advanced (Stages III-IV) disease. Survival of patients diagnosed with ovarian cancer is known to closely correlate with stage at diagnosis.

Treatment for advanced ovarian carcinoma is based on the combination of surgery and chemotherapy. The objective of surgical intervention in patients suffering from advanced disease is to perform cytoreduction to minimal residual disease in the abdominal cavity. Surgery is followed by adjuvant platinum based chemotherapy. The two most important prognostic factors for patients with advanced ovarian carcinoma are the amount of residual disease left after surgery and the response to platinum based chemotherapy.

Platinum-based cytotoxic chemotherapy in conjunction with debulking surgery is currently the gold standard treatment for patients with ovarian cancer. Although 80-90% of patients initially respond to first line treatment, most will either later progress during therapy or recur after complete remission.

microRNAs (miRNAs, miRs) are endogenous non-coding small RNAs that interfere with the translation of coding messenger RNAs (mRNAs) in a sequence specific manner, playing a critical role in the control of gene expression during development and tissue homeostasis (Yi et al., 2006, Nat Genet 38, 356-362). Certain miRNAs have been shown to be deregulated in human cancer, and their specific over- or under-expression has been shown to correlate with particular tumor types (Calin and Croce, 2006, Nat Rev Cancer 6, 857-866), as well as to predict patient outcome (Yu et al., 2008, Cancer Cell 13, 48-57).

In spite of considerable research into therapies for ovarian cancer, ovarian cancer remains difficult to diagnose and treat effectively, and the mortality observed in patients indicates that improvements are needed in the treatment and prevention of the disease.

SUMMARY OF THE INVENTION

The present invention is based in part on the development of microRNA inhibitors, to be used for the treatment of ovarian cancer patients. The microRNA inhibitors were shown to inhibit specific microRNAs that are involved in proliferation of ovarian cells, and therefore reduce cell proliferation. According to some embodiments, the target cells are residual ovarian cancer cells in the abdominal cavity where most ovarian cancer metastasis occur.

In order to develop a microRNA-based treatment for ovarian cancer, candidate microRNA targets were identified for inhibition. microRNAs that were over-expressed in ovarian tissue (both tumor, metastases and normal) as compared to other normal tissues were chosen, as well as highly expressed microRNAs. Candidates having a greater potential of being a drug target were further selected, using a proliferation assay for cells treated with a specific microRNA inhibitor.

According to some aspects, the present invention provides a method of inhibiting proliferation of ovarian cancer cells, the method comprising introducing into the cells a compound which inhibit expression or activity of a nucleic acid sequence selected from the group consisting of SEQ ID NOs: 1-40 and sequences at least about 80% identical thereto.

According to some embodiments, said compound comprising a modified oligonucleotide consisting of 15 to 30 linked nucleosides, wherein the modified oligonucleotide has a nucleobase sequence that is complementary to a nucleobase sequence selected from SEQ ID NOs: 1-40; or to a sequence at least 80% identical thereto.

According to some embodiments, said modified oligonucleotide has a nucleobase sequence selected from SEQ ID NOs: 41-58; or to a sequence at least 80% identical thereto.

According to one embodiment, the ovarian cancer cell is selected from the group consisting of serous and endometrioid ovarian cancer.

According to other aspects, the present invention provides a method for treating ovarian cancer, comprising administering to a subject in need thereof a pharmaceutical composition comprising a modified oligonucleotide consisting of 15 to 30 linked nucleosides, wherein the modified oligonucleotide has a nucleobase sequence that is complementary to a nucleobase sequence selected from SEQ ID NOs: 1-40; or to a sequence at least 80% identical thereto.

In certain embodiments, the modified oligonucleotide has a nucleobase sequence comprising at least 15 contiguous nucleobases of a nucleobase sequence selected from among the nucleobase sequences recited in SEQ ID NOs: 41-58; or a sequence at least 80% identical thereto.

In certain embodiments, the subject is a human.

In certain embodiments, the present invention provides a pharmaceutical composition comprising a modified oligonucleotide of the invention or a salt thereof and a pharmaceutically acceptable carrier or diluent.

In certain embodiments, the compound consists of a modified oligonucleotide.

In certain embodiments, the modified oligonucleotide consists of 15, 16, 17, 18, 19, 20, 21, 22, 23, 24, or 25 linked nucleosides.

In certain embodiments, the nucleobase sequence of the modified oligonucleotide has no more than two mismatches to a nucleobase sequence selected from SEQ ID NO: 41-58. In certain embodiments, the nucleobase sequence of the modified oligonucleotide has no more than one mismatch to a nucleobase sequence selected from SEQ ID NO: 41-58. In certain embodiments, the nucleobase sequence of the modified oligonucleotide has one mismatch to a nucleobase sequence selected from SEQ ID NO: 41-58. In certain embodiments, the nucleobase sequence of the modified oligonucleotide has no mismatches to a nucleobase sequence selected from SEQ ID NO: 41-58.

In certain embodiments, the modified oligonucleotide comprises one or more modified sugars, internucleoside linkages, or nucleobases. In certain embodiments, at least one internucleoside linkage is a modified internucleoside linkage. For example, at least one internucleoside linkage may be a phosphorothioate internucleoside linkage. In certain embodiments, each internucleoside linkage is a modified internucleoside linkage. For example, each internucleoside linkage may be a phosphorothioate internucleoside linkage.

In certain embodiments, at least one nucleoside of the modified oligonucleotide comprises a modified sugar. In certain embodiments, each of a plurality of nucleosides comprises a modified sugar. In certain embodiments, each nucleoside of the modified oligonucleotide comprises a modified sugar. In each of these embodiments, the modified sugar may be a 2'-O-methoxyethyl sugar, a 2'-fluoro sugar, a 2'-O-methyl sugar, or a bicyclic sugar moiety. In certain embodiments, each of a plurality of nucleosides comprises a 2'-O-methoxyethyl sugar and each of a plurality of nucleosides comprises a 2'-fluoro sugar.

In certain embodiments, the modified oligonucleotide comprises at least one modified nucleobase. In certain such embodiments, the modified nucleobase is a 5-methyleytosine. In certain embodiments, at least one nucleoside comprises a cytosine, wherein the cytosine is a 5-methylcytosine. In certain such embodiments, each cytosine is a 5-methylcytosine.

In certain embodiments, administration of a compound of the invention comprises intravenous administration, subcutaneous administration, intratumoral administration, or chemoembolization.

In certain embodiments, the methods of the present invention further comprise administering at least one additional therapy. The additional therapy may be a chemotherapeutic agent. The chemotherapeutic agent may be selected from cisplatin, carboplatin, camptothecins, doxorubicin, cyclophosphamide, paclitaxel, etoposide, vinblastine, Actinomycin D and cloposide. The additional therapy may be administered at the same time, less frequently, or more frequently than a compound or pharmaceutical composition of the invention.

In certain embodiments, the modified oligonucleotide is administered at a dose selected from 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, and 800 mg. The modified oligonucleotide may be administered one per day, once per week, once per two weeks, once per three weeks, or once per four weeks.

In certain embodiments, the administration of a compound of the invention results in reduction of ovarian tumor size. In certain embodiments, the administration of a compound of the invention prevents an increase in tumor size and/or tumor number. In certain embodiments, the administration of a compound of the invention prevents, slows, and/or stops metastatic progression. In certain embodiments, the administration of a compound of the invention extends the overall survival time of the subject. In certain embodiments, the administration of a compound of the invention extends the progression-free survival of the subject. In certain embodiments, administration of a compound of the invention prevents the recurrence of ovarian tumors. In certain embodiments, administration of a compound of the invention prevents recurrence of ovarian tumor metastasis.

According to some embodiments the composition is suitable for administration in combination with at least one other anticancer agent in unit dosage form. According to some embodiments the anticancer agent is selected from the group consisting of cisplatin, carboplatin, camptothecins, doxorubicin, cyclophosphamide, etoposide, vinblastine, Actinomycin D, paclitaxel and cloposide.

These and other embodiments of the present invention will become apparent in conjunction with the figures, description and claims that follow.

DETAILED DESCRIPTION

Figure 1A:
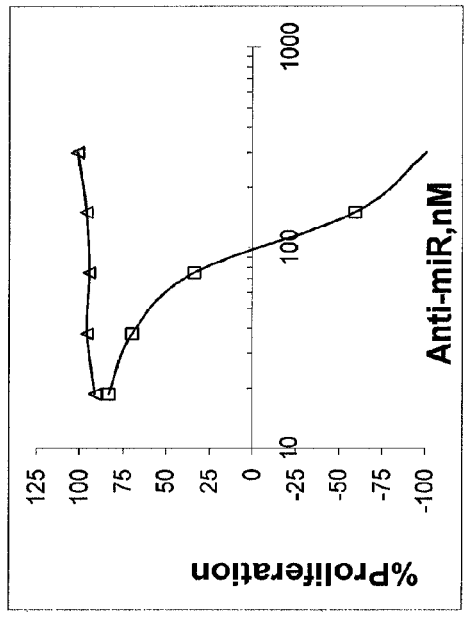
FIGS. 1A-1D demonstrate the effect of anti-miR (nM) (squares) on proliferation (percentage) of OVCAR-3 cells, 72 hours after transfection as compared to negative control anti-miR (triangles). 1A-anti-miR-103 (SEQ ID NO: 42), 1B-anti-miR-100 (SEQ ID NO: 41), 1C-anti-miR-125b (SEQ ID NO: 43), 1D-anti-miR-191 (SEQ ID NO: 46).

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can command go, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

1. DEFINITIONS a. Administering

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intratumoral administration" means administration within a tumor.

"Chemoembolization" means a procedure in which the blood supply to a tumor is blocked surgically or mechanically and chemotherapeutic agents are administered directly into the tumor.

b. Chemotherapeutic Agent

A drug used to treat a disease, especially cancer. In relation to cancer the drugs typically target rapidly dividing cells, such as cancer cells. Non-limiting examples of chemotherapeutic agents include cisplatin, carboplatin, camptothecins, doxorubicin, cyclophosphamide, paclitaxel, etoposide, vinblastine, Actinomycin D and cloposide.

c. Complement

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

d. Detection

"Detection" means detecting the presence of a component in a sample. Detection also means detecting the absence of a component. Detection also means measuring the level of a component, either quantitatively or qualitatively.

e. Differential Expression

"Differential expression" may mean qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type that may be detectable by standard techniques. Some genes will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, and RNase protection.

f. Dose

"Dose" as used herein means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

g. Dosage Unit

"Dosage unit" as used herein means a form in which a pharmaceutical agent is provided. In certain embodiments, a dosage unit is a vial containing lyophilized oligonucleotide. In certain embodiments, a dosage unit is a vial containing reconstituted oligonucleotide.

h. Expression Profile

"Expression profile" as used herein may mean a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cRNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of, including all of the listed nucleic acid sequences. The term "expression profile" may also mean measuring the abundance of the nucleic acid sequences in the measured samples.

i. Gene

"Gene" used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

j. Identity

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

k. Inhibit

"Inhibit" as used herein may mean prevent, suppress, repress, reduce or eliminate.

l. Label

"Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

m. Metastasis

"Metastasis" as used herein means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

n. Mismatch

"Mismatch" means a nucleobase of a first nucleic acid that is not capable of pairing with a nucleobase at a corresponding position of a second nucleic acid.

o. Nucleic Acid

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

p. Overall Survival Time

"Overall survival time" or "survival time", as used herein means the time period for which a subject survives after diagnosis of or treatment for a disease. In certain embodiments, the disease is cancer.

q. Progression-Free Survival

"Progression-free survival" means the time period for which a subject having a disease survives, without the disease getting worse. In certain embodiments, progression-free survival is assessed by staging or scoring the disease. In certain embodiments, progression-free survival of a subject having cancer is assessed by evaluating tumor size, tumor number, and/or metastasis.

r. Probe

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

s. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

t. Selectable Marker

"Selectable marker" as used herein means any gene which confers a phenotype on a host cell in which it is expressed to facilitate the identification and/or selection of cells which are transfected or transformed with a genetic construct. Representative examples of selectable markers include the ampicillin-resistance gene ($Amp^r$), tetracycline-resistance gene ($Tc^r$), bacterial kanamycin-resistance gene ($Kan^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein (GFP)-encoding gene and luciferase gene.

u. Stringent Hybridization Conditions

"Stringent hybridization conditions" used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

v. Substantially Complementary

"Substantially complementary" used herein may mean that a first sequence is at least 60%-99% identical to the complement of a second sequence over a region of 8-50 or more nucleotides, or that the two sequences hybridize under stringent hybridization conditions.

w. Substantially Identical

"Substantially identical" used herein may mean that a first and second sequence are at least 60%-99% identical over a region of 8-50 or more nucleotides or amino acids, or with respect to nucleic acids, if the first sequence is substantially complementary to the complement of the second sequence.

x. Subject

As used herein, the term "subject" refers to a mammal, including both human and other mammals. The methods of the present invention are preferably applied to human subjects.

y. Therapeutically Effective Amount

"Therapeutically effective amount" or "therapeutically efficient" used herein as to a drug dosage, refer to dosage that provides the specific pharmacological response for which the drug is administered in a significant number of subjects in need of such treatment. The "therapeutically effective amount" may vary according, for example, the physical condition of the patient, the age of the patient and the severity of the disease.

z. therapy

"Therapy" as used herein means a disease treatment method. In certain embodiments, therapy includes, but is not limited to, chemotherapy, surgical resection, transplant, and/or chemoembolization.

aa. Treat

"Treat" or "treating" used herein when referring to protection of a subject from a condition may mean preventing, suppressing, repressing, or eliminating the condition. Preventing the condition involves administering a composition described herein to a subject prior to onset of the condition. Suppressing the condition involves administering the composition to a subject after induction of the condition but before its clinical appearance. Repressing the condition involves administering the composition to a subject after clinical appearance of the condition such that the condition is reduced or prevented from worsening. Elimination of the condition involves administering the composition to a subject after clinical appearance of the condition such that the subject no longer suffers from the condition.

bb. Unit Dosage Form

"Unit dosage form," used herein may refer to a physically discrete unit suitable as a unitary dosage for a human or animal subject. Each unit may contain a predetermined quantity of a composition described herein, calculated in an amount sufficient to produce a desired effect in association with a pharmaceutically acceptable diluent, carrier or vehicle. The specifications for a unit dosage form may depend on the particular composition employed and the effect to be achieved, and the pharmacodynamics associated with the composition in the host.

cc. Variant

"Variant" used herein to refer to a nucleic acid may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

dd. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. TREATMENT OF OVARIAN CANCER, ITS STAGES, AND HISTOLOGICAL SUBTYPES

The treatment of ovarian cancer is based on the stage of the disease which is a reflection of the extent or spread of the cancer to other parts of the body. Staging is performed when the ovarian cancer is removed. During the surgical procedure biopsies are obtained from various sites in the abdominal cavity. During this procedure, depending on the stage of the disease, the surgeon will either remove just the ovary and fallopian tube or will remove ovaries, fallopian tubes and uterus. In addition, the surgeon will attempt to remove as much of the cancer as possible. Ovarian cancer is staged as follows:

Stage I cancer is confined to one or both ovaries. The cancer is Stage II if either one or both of the ovaries is involved and has spread to the uterus and/or the fallopian tubes or other sites in the pelvis. The cancer is Stage III cancer if one or both of the ovaries is involved and has spread to lymph nodes or other sites outside of the pelvis but is still within the abdominal cavity, such as the surface of the intestine or liver. The cancer is Stage IV cancer if one or both ovaries are involved and the cancer has spread outside the abdomen or to the inside of the liver.

The primary treatment of ovarian cancer is surgery at which time the cancer is removed from the ovary and from as many other sites as is possible. Chemotherapy is the second treatment modality. Another treatment modality is radiation, which is used in only certain instances. The treatment of ovarian cancer depends on the stage of the disease, the histological cell type, and the patient's age and overall condition. The histological cell type and the extent of disease based on the biopsies performed during surgery.

Over 75% of ovarian cancers cases are diagnosed at an advanced stage. Overall 5-year survival in ovarian epithelial carcinoma is low because of the preponderance of late-stage disease at diagnosis. The overall 5-year survival rate, according to stages, is:
a. Stage I and II: 80-100%
b. Stage III: 15-20%
c. Stage IV: 5%

Ovarian cancer is classified according to the histology of the tumor. Histology dictates many aspects of clinical treatment, management, and prognosis. Surface epithelial-stromal tumor, also known as ovarian epithelial carcinoma, is the most common type of ovarian cancer. It includes serous tumor (including serous papillary cystadenocarcinoma), endometrioid tumor and mucinous cystadenocarcinoma.

3. MICRORNAS AND THEIR PROCESSING

A gene coding for a miRNA may be transcribed leading to production of a miRNA precursor known as the primiRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 30-200 nt precursor known as the pre-miRNA. Drosha may cleave the pri-miRNA with a staggered cut typical of Rnase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an Rnase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for miR-196 and Hox B8 and it was further shown that miR-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PloS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8, the "seed", were used to identify and validate targets. MiRNAs differ in their basic structure and sequence of nucleotides; however similarity in seed sequence may suggest similar activity.

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

4. NUCLEIC ACIDS

Nucleic acids are provided herein. The nucleic acid may comprise the sequence of SEQ ID NOS: 1-58 presented in table 1 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

TABLE 1

| Target miR | MiR SEQ ID NO: | Hairpin SEQ ID NO: | External ID | Antisense oligo Sequence | Antisense SEQ ID NO: |
|---|---|---|---|---|---|
| hsa-miR-100 | 1 | 19 | 36858359 | CACAAGUUCGGA UCUACGGGUU | 41 |
| hsa-miR-103 | 2 | 20, 21 | 36858360 | UCAUAGCCCUGU ACAAUGCUGCU | 42 |
| hsa-miR-125b | 3 | 22, 23 | 36858363 | UCACAAGUUAGG GUCUCAGGGA | 43 |
| hsa-miR-17 | 4 | 24 | 60432524 | CUACCUGCACUG UAAGCACUUUG | 44 |
| hsa-miR-18a | 5 | 25 | 60432525 | CUAUCUGCACUA GAUGCACCUUA | 45 |
| hsa-miR-191 | 6 | 26 | 36858368 | CAGCUGCUUUUG GGAUUCCGUUG | 46 |
| hsa-miR-20b | 7 | 27 | 36641194 | CUACCUGCACUA UGAGCACUUUG | 47 |
| hsa-miR-21 | 8 | 28 | 36858370 | UCAACAUCAGUC UGAUAAGCUA | 48 |
| hsa-miR-210 | 9 | 29 | 36858371 | UCAGCCGCUGUC ACACGCACAG | 49 |
| hsa-miR-22 | 10 | 30 | 36858373 | ACAGUUCUUCAA CUGGCAGCUU | 50 |
| hsa-miR-221 | 11 | 31 | 36858374 | GAAACCCAGCAG ACAAUGUAGCU | 51 |
| hsa-miR-23a | 12 | 32 | 36858376 | GGAAAUCCCUGG CAAUGUGAU | 52 |
| hsa-miR-24 | 13 | 33, 34 | 36858377 | CUGUUCCUGCUG AACUGAGCCA | 53 |
| hsa-miR-25 | 14 | 35 | 60432527 | UCAGACCGAGAC AAGUGCAAUG | 54 |
| hsa-miR-26a | 15 | 36, 37 | 36858378 | AGCCUAUCCUGG AUUACUUGAA | 55 |
| hsa-miR-27a | 16 | 38 | 38548308 | GCGGAACUUAGC CACUGUGAA | 56 |
| hsa-miR-31 | 17 | 39 | 36858379 | AGCUAUGCCAGC AUCUUGCCU | 57 |
| hsa-miR-99a | 18 | 40 | 36858385 | CACAAGAUCGGA UCUACGGGUU | 58 |

Nucleic Acid Complex

The nucleic acid may further comprise one or more of the following: a peptide, a protein, a RNA-DNA hybrid, an antibody, an antibody fragment, a Fab fragment, and an aptamer. The nucleic acid may also comprise a protamine-antibody fusion protein as described in Song et at (Nature Biotechnology 2005; 23:709-17) and Rossi (Nature Biotechnology 2005: 23; 682-4), the contents of which are incorporated herein by reference. The protamine-fusion protein may comprise the abundant and highly basic cellular protein protamine. The protamine may readily interact with the nucleic acid. The protamine may comprise the entire 51 amino acid protamine peptide or a fragment thereof. The protamine may be covalently attached to another protein, which may be a Fab. The Fab may bind to a receptor expressed on a cell surface.

Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-40 or variants thereof.

The pri-miRNA may form a hairpin structure. The hairpin may comprise first and second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

Pre-miRNA

The nucleic acid may also comprise a sequence of a pre-miRNA or a variant thereof. The pre-miRNA sequence may comprise from 45-200, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-40 or variants thereof.

MiRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-18, or variants thereof.

Anti-miRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA. The sequence of the anti-miRNA may comprise the compliment of SEQ ID NOS: 1-18, or variants thereof.

5. PROBES

A probe is also provided comprising a nucleic acid described herein. Probes may be used for screening and diagnostic methods. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

6. BIOCHIP

A biochip is also provided. The biochip may comprise a solid substrate comprising an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

7. THERAPEUTIC

A method for treating a disease or disorder associated with ovarian cancer is also provided. Furthermore, existing miRNA molecules may be used as starting materials for the manufacture of sequence-modified anti-miRNA molecules. As previously discussed the methods, compositions and articles of manufacture of the present invention are particularly useful in the treatment of cancer.

The compositions of the present invention may be combined with a chemotherapeutic agent, a combination of chemotherapeutic agents and/or radiotherapy.

Cancer treatments often comprise more than one therapy. As such, in certain embodiments the present invention provides methods for treating cancer comprising administering to a subject in need thereof the composition of the present invention, and further comprising administering at least one additional therapy.

In certain embodiments, an additional therapy may also be designed to treat cancer. An additional therapy may be a chemotherapeutic agent. Suitable chemotherapeutic agents include cisplatin, carboplatin, camptothecins, doxorubiein, cyclophosphamide, paclitaxel, etoposide, vinblastine, Actinomycin D and cloposide An additional therapy may be surgical resection of tumor(s), or chemoembolization.

8. COMPOSITIONS

A pharmaceutical composition is also provided. The composition may comprise a nucleic acid described herein and optionally a pharmaceutically acceptable carrier. The composition may encompass modified oligonucleotides that are identical, substantially identical, substantially complementary or complementary to any nucleobase sequence version of the miRNAs or nucleic acids described herein or a precursor thereof.

The compositions may be used for therapeutic applications. The pharmaceutical composition may be administered by known methods, including wherein a nucleic acid is introduced into a desired target cell in vitro or in vivo.

Methods for the delivery of nucleic acid molecules are described in Akhtar et al., (Trends Cell Bio. 2, 139, 1992). WO 94/02595 describes general methods for delivery of RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. More detailed descriptions of nucleic acid delivery and administration are provided for example in WO93/23569, WO99/05094, and WO99/04819.

The nucleic acids can be introduced into tissues or host cells by any number of routes, including viral infection, microinjection, or fusion of vesicles. Jet injection may also be used for intra-muscular administration, as described by Furth et al. (Anal Biochem 115 205:365-368, 1992). The nucleic acids can be coated onto gold microparticles, and delivered intradermally by a particle bombardment device, or "gene gun" as described in the literature (see, for example, Tang et al. Nature 356:152-154, 1992), where gold microprojectiles are coated with the DNA, then bombarded into skin cells.

The compositions of the present invention can be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc.

In certain embodiments, a pharmaceutical composition of the present invention is administered in the form of a dosage unit (e.g., tablet, capsule, bolus, etc.). In certain embodiments, such pharmaceutical compositions comprise a modified oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of a modified oligonucleotide which has been prepared in water for injection, or in saline for injection, adjusted to pH 7.0-9.0 with acid or base during preparation, and then lyophilized. The lyophilized modified oligonucleotide may be 25-800 mg of a modified oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In certain embodiments, pharmaceutical compositions of the present invention comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds comprising modified oligonucleotides with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject.

In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition of the present invention comprises a modified oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides of the present invention are formulated as a prodrug. In certain embodiments, upon in vivo administration, a prodrug is chemically converted to the biologically, pharmaceutically or therapeutically more active form of a modified oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Having now generally described the invention, the same will be more readily understood through reference to the following examples, which are provided by way of illustration and are not intended to be limiting of the present invention.

EXAMPLES

Example 1

Materials and Methods a. Patients and Samples

Patients, who were surgically treated for ovarian cancer at the Rabin Medical Center between January, 2000 and December, 2004 were identified. All pathology slides were re-evaluated by an expert pathologist. Tumor histology was established and the diagnosis of EOC was confirmed. Only serous papillary and endometrioid histology were included in the study. Patients found to have a synchronous endometrial malignancy were excluded. For each patient, a formalin-fixed paraffin embedded (FFPE) tumor sample was obtained and tumor cell content was evaluated by a pathologist. Only tumor samples with a minimum of 50% tumor tissue content were included. Patient charts were reviewed for clinicopathologic information—demographics, surgical procedure and findings, pathology, chemotherapy regimens and response, follow-up and survival. Optimal surgical cytoreduction was defined during the study period as the largest residual tumor diameter of 1 cm.

21 samples from ovarian tumor and 19 samples from ovarian metastases were compared to 53 different normal tissues of which 18 were normal tissue of the abdominal area (including: colon, liver, small intestine, fallopian tubes, endometrium, Small intestine-Deudenum, Small intestine-Jejunum, Stomach, and Spleen) for their miR expression. Comparison was also made to normal ovarian tissues. Normal samples were purchased from Ambion.

b. RNA Extraction

For FFPE samples, total RNA was isolated from seven to ten 10-μm-thick tissue sections using the microRNA extraction protocol developed at Rosetta Genomics. Briefly, the sample is incubated a few times in Xylene at 57° to remove paraffin excess, followed by Ethanol washes. Proteins are degraded by proteinase K solution at 45° C. for few hours. The RNA is extracted with acid phenol:chloroform followed by ethanol precipitation and DNAse digestion. Total RNA quantity and quality is checked by spectrophotometer (Nanodrop ND-1000).

c. microRNA Microarray Platform

Custom microarrays were produced by printing DNA oligonucleotide probes representing 903 human microRNAs. Each probe, printed in triplicate, carries up to 22-nt linker at the 3' end of the microRNA's complement sequence in addition to an amine group used to couple the probes to coated glass slides. 20 μM of each probe were dissolved in 2×SSC+0.0035% SDS and spotted in triplicate on Schott Nexterion® Slide E coated microarray slides (Mainz, Germany) using a Genomic Solutions® BioRobotics MicroGrid II according the MicroGrid manufacturer's directions. 22 negative control probes were designed using the sense sequences of different microRNAs. Two groups of positive control probes were designed to hybridize to the microarray (i) synthetic small RNA were spiked to the RNA before labeling to verify the labeling efficiency and (ii) probes for abundant small RNA (e.g. small nuclear RNAs (U43, U49, U24, Z30, U6, U48, U44), 5.8 s and 5 s ribosomal RNA) are spotted on the array to verify RNA quality. The slides were blocked in a solution containing 50 mM ethanolamine, 1M Tris (pH9.0) and 0.1% SDS for 20 min at 50° C., then thoroughly rinsed with water and spun dry.

d. Cy-Dye Labeling of microRNA for Microarray

Five μg of total RNA were labeled by ligation (Thomson et al., Nature Methods 2004, 1:47-53) of an RNA-linker, p-rCrU-Cy/dye (Dharmacon, Lafayette), to the 3'-end with Cy3 or Cy5. The labeling reaction contained total RNA, spikes (0.1-20 fmoles), 400 ng RNA-linker-dye, 15% DMSO, 1× ligase buffer and 20 units of T4 RNA ligase (NEB) and proceeded at 4° C. for 1 hr followed by 1 hr at 37° C. The labeled RNA was mixed with 3× hybridization buffer (Ambion), heated to 95° C. for 3 min and then added on top of the microarray. Slides were hybridized 12-16 hr in 42° C., followed by two washes in room temperature with 1×SSC and 0.2% SDS and a final wash with 0.1×SSC.

Arrays were scanned using an Agilent Microarray Scanner Bundle G2565BA (resolution of 10 μm at 100% and 10% power). Array images were analyzed using SpotReader software (Niles Scientific).

e. Data Analysis

Triplicate spots were combined to produce one signal for each probe by taking the logarithmic mean of reliable spots. All data was log-transformed (natural base) and the analysis was performed in log-space. A reference data vector for normalization R was calculated by taking the median expression level for each probe across all samples. For each sample data vector S, a 2nd degree polynomial F was found so as to provide the best fit between the sample data and the reference data, such that R≈F(S). Remote data points ("outliers") were not used for fitting the polynomial F. For each probe in the sample (element $S_i$ in the vector 5), the normalized value (in log-space) $M_i$ was calculated from the initial value $S_i$ by transforming it with the polynomial function F, so that $M_i=(S_i)$.

f. Cell Culture Maintenance and Transfections

OVCAR-3 and SKOV-3 cell lines were purchased from NCI. Cells were grown under standard growth conditions. Transfection of cells with anti-miRs was conducted using Oligofectamine (Invitrogen, Cat#12252011), according to manufacturer instructions. Briefly, cells were exposed to anti-miR and transfection reagent complex in OptiMEM for 4 h. After that transfection media was removed and full supplemented media was applied.

g. Proliferation Assays 72 h after transfection, cells were tested for proliferation using cell Proliferation Assay kit-cellTiter 96 AQueous One solution (Promega, Cat# G3581), according to manufacture instructions. Absorbance was measured at 490 nm, using ELx808 ultra microplate reader (BIO-TEK instruments, INC). Absorbance was blanked using medium and calculated as % of untreated cells. At day of transfection another plate with non-treated cells were also tested for proliferation. This result was subtracted from the 72 h read, so proliferation is calculated from the time of transfection.

h. Anti-miR Molecules

2'-O-Me modified Antisense oligonucleotides having the sequence of the reverse complement of the relevant miRs were ordered from IDT.

Example 2

Expression Analysis

Comparison of ovarian (tumors and metastases) samples to normal abdominal tissues and to normal ovarian tissues resulted with a list of upregulated or highly expressed miRs. Table 2 discloses the list of miRs that were later shown to be important in cell proliferation inhibition by anti-miRs.

TABLE 2

| miRname | Signal in Tumor | Signal in Normal tissue | fold-change | p-value | Reason for election |
|---|---|---|---|---|---|
| hsa-miR-100 | 9800 | 3400 | 2.91(+) | 0.0000061 | differentially expressed - upregulated in cancer |
| hsa-miR-17 | 4600 | 2100 | 2.16(+) | 4.4E−09 | differentially expressed - upregulated in cancer |
| hsa-miR-18a | 760 | 160 | 4.61(+) | 3.9E−09 | differentially expressed - upregulated in cancer |
| hsa-miR-21 | 70000 | 32000 | 2.17(+) | 5.1E−11 | differentially expressed - upregulated in cancer |
| hsa-miR-210 | 2300 | 340 | 6.70(+) | 9.1E−13 | differentially expressed - upregulated in cancer |
| hsa-miR-24 | 31000 | 15000 | 2.09(+) | 2.4E−13 | differentially expressed - upregulated in cancer |
| hsa-miR-25 | 2000 | 880 | 2.29(+) | 0.00000078 | differentially expressed - upregulated in cancer |

TABLE 2-continued

| miRname | Signal in Tumor | Signal in Normal tissue | fold-change | p-value | Reason for election |
|---|---|---|---|---|---|
| hsa-miR-27a | 17000 | 6400 | 2.66(+) | 1.3E−10 | differentially expressed - upregulated in cancer |
| hsa-miR-99a | 16000 | 3800 | 4.18(+) | 0.000016 | differentially expressed - upregulated in cancer |
| hsa-mir-103 | 14000 | 8600 | 1.62 (+) | 0.0011 | differentially expressed - upregulated in cancer |
| hsa-mir-22 | 5500 | 2500 | 2.18 (+) | 0.0034 | differentially expressed - upregulated in cancer |
| hsa-mir-221 | 12000 | 7700 | 1.59 (+) | 0.00041 | differentially expressed - upregulated in cancer |
| hsa-mir-23a | 30000 | 16000 | 1.84 (+) | 0.00025 | differentially expressed - upregulated in cancer |
| hsa-mir-26a | 31000 | 22000 | 1.43 (+) | 0.013 | differentially expressed - upregulated in cancer |
| hsa-mir-31 | 2700 | 720 | 3.73 (+) | 0.043 | differentially expressed - upregulated in cancer |
| hsa-mir-125b | 30000 | 50000 | 1.69 (−) | 0.038 | Highly expressed in ovarian tissue |
|  | 30000 | 25000 | 1.17 (+) | 0.76 |  |
| hsa-mir-20b | 650 | 160 | NA | NA | differentially expressed - upregulated in cancer |
| hsa-mir-191 | 7100 | 6200 | 1.15 (+) | 0.45 | Highly expressed in ovarian tissue |
|  | 7100 | 7000 | 1.02 (+) | 0.85 |  |

Example 3

Proliferation Assays

Figure 1B:
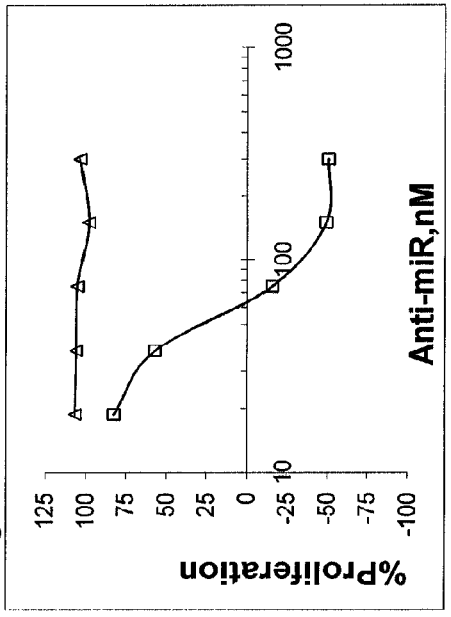
Figure 1C:
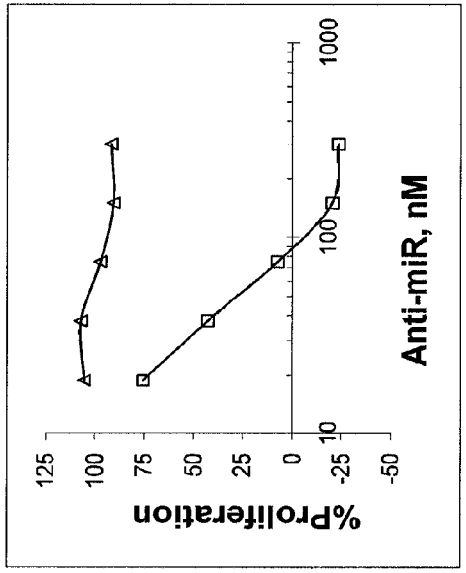
Figure 1D:
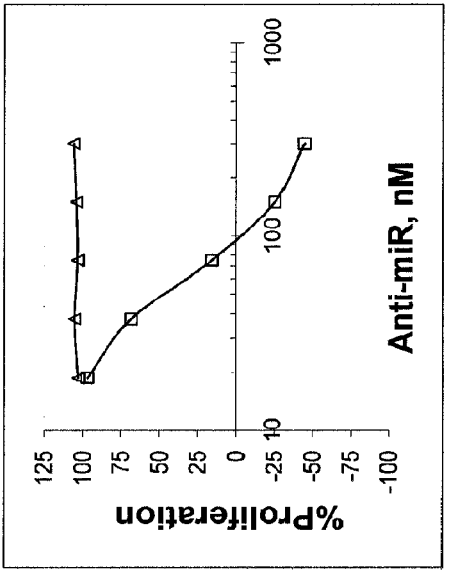
Figure 2A:
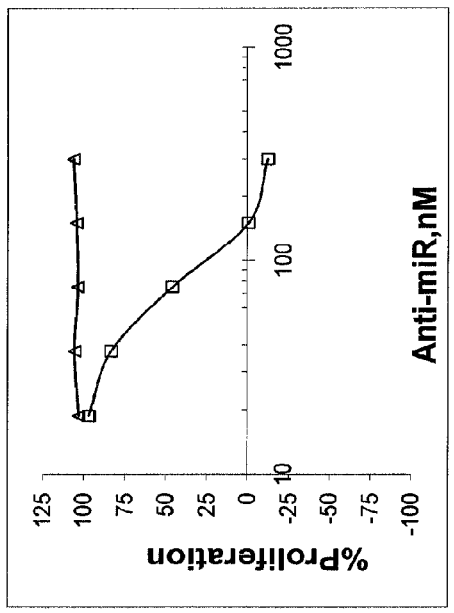
FIGS. 2A-2D demonstrate the effect of anti-miR (nM) (squares) on proliferation (percentage) of OVCAR-3 cells, 72 hours after transfection as compared to negative control anti-miR (triangles). 2A-anti-miR-21 (SEQ ID NO: 48), 2B-anti-miR-210 (SEQ ID NO: 49), 2C-anti-miR-221 (SEQ ID NO: 51), 2D-anti-miR-99a (SEQ ID NO: 58).
Figure 2B:
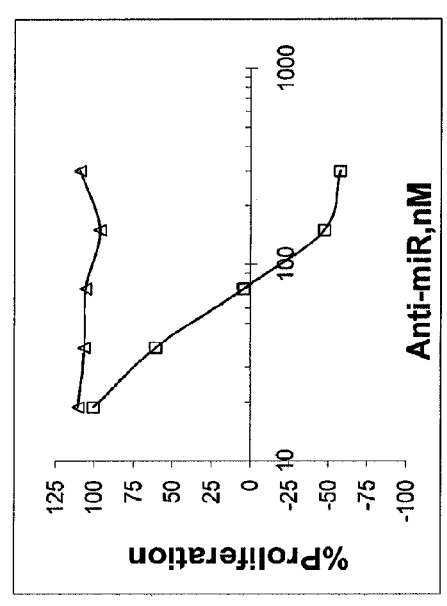
Figure 2C:
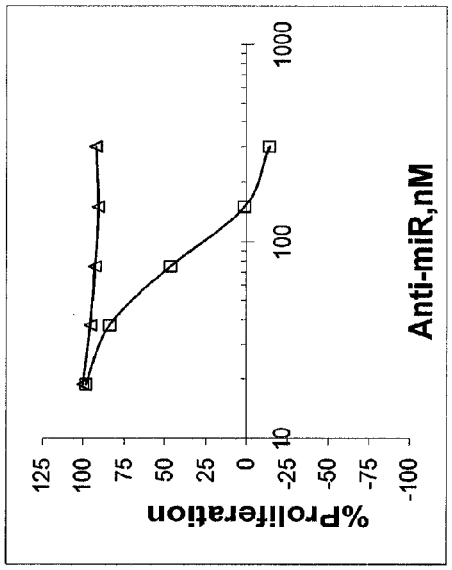
Figure 2D:
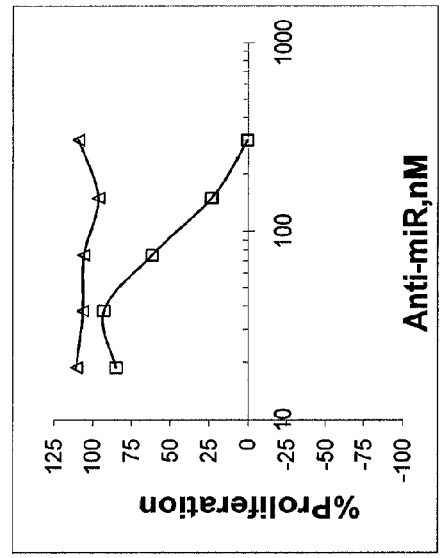
Figure 3A:
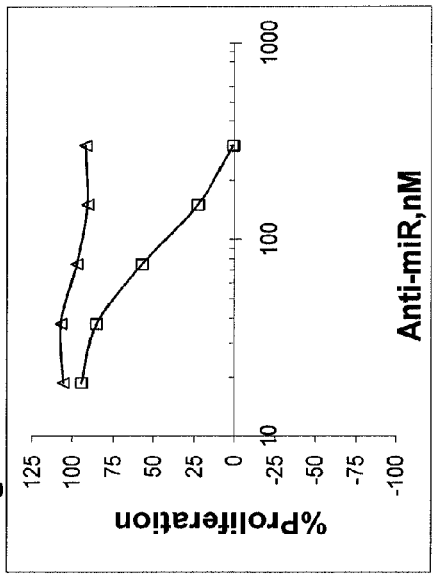
FIGS. 3A-3D demonstrate the effect of anti-miR (nM) (squares) on proliferation (percentage) of OVCAR-3 cells, 72 hours after transfection as compared to negative control anti-miR (triangles). 3A-anti-miR-24 (SEQ ID NO: 53), 3B-anti-miR-25 (SEQ ID NO: 54), 3C-anti-miR-26a (SEQ ID NO: 55), 3D-anti-miR-27a (SEQ ID NO: 56).
Figure 3B:
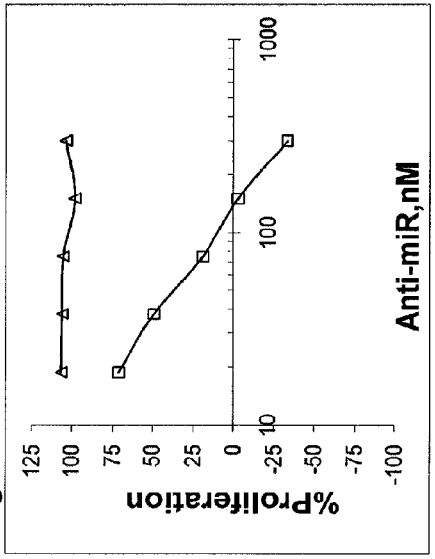
Figure 3C:
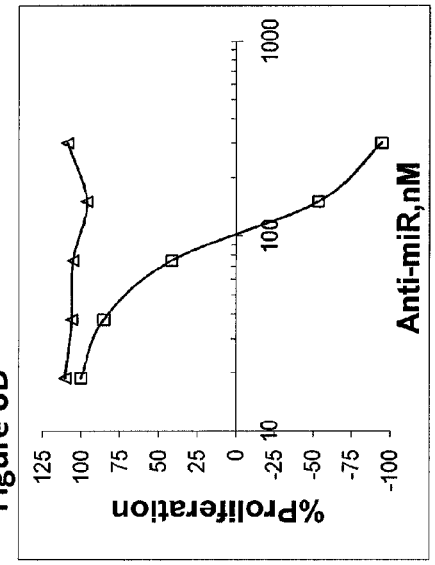
Figure 3D:
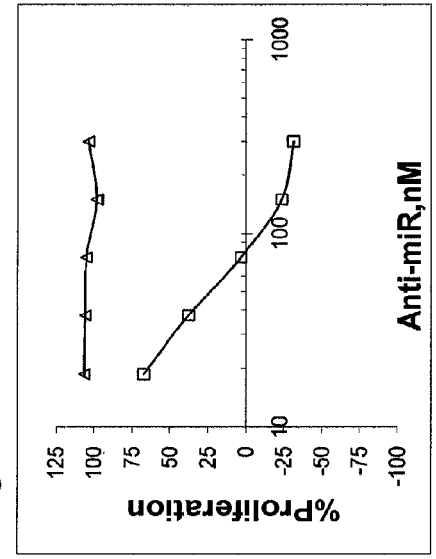
Figure 4B:
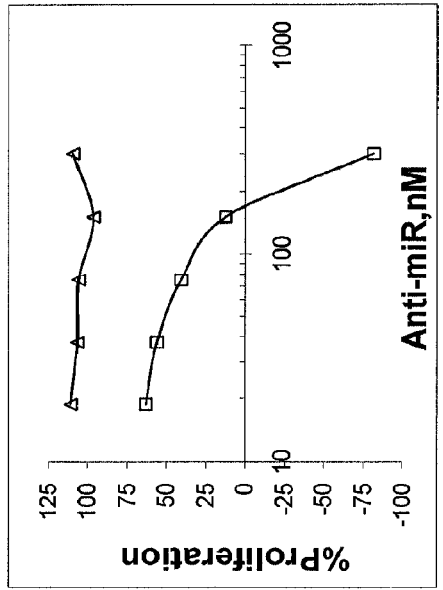
FIGS. 4A-4D demonstrate the effect of anti-miR (nM) (squares) on proliferation (percentage) of OVCAR-3 cells, 72 hours after transfection as compared to negative control anti-miR (triangles). 4A-anti-miR-18a (SEQ ID NO: 45), 4B-anti-miR-20b (SEQ ID NO: 47), 4C-anti-miR-31 (SEQ ID NO: 57), 4D-anti-miR-23a (SEQ ID NO: 52).
Figure 4A:
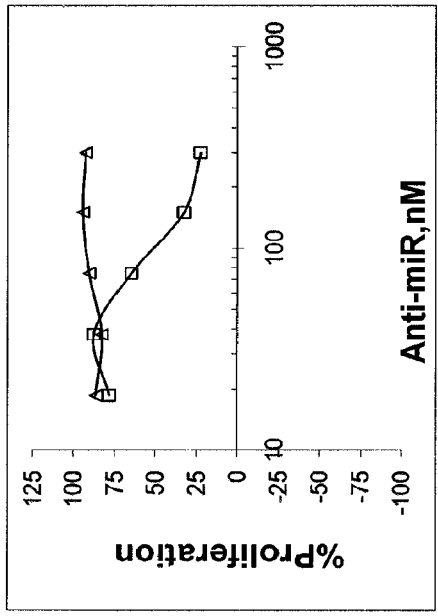
Figure 4D:
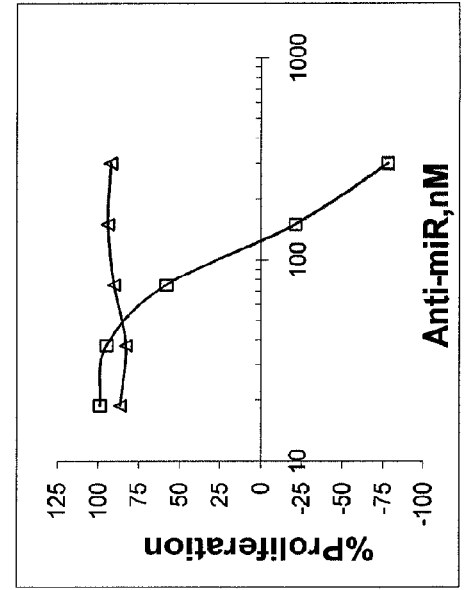
Figure 4C:
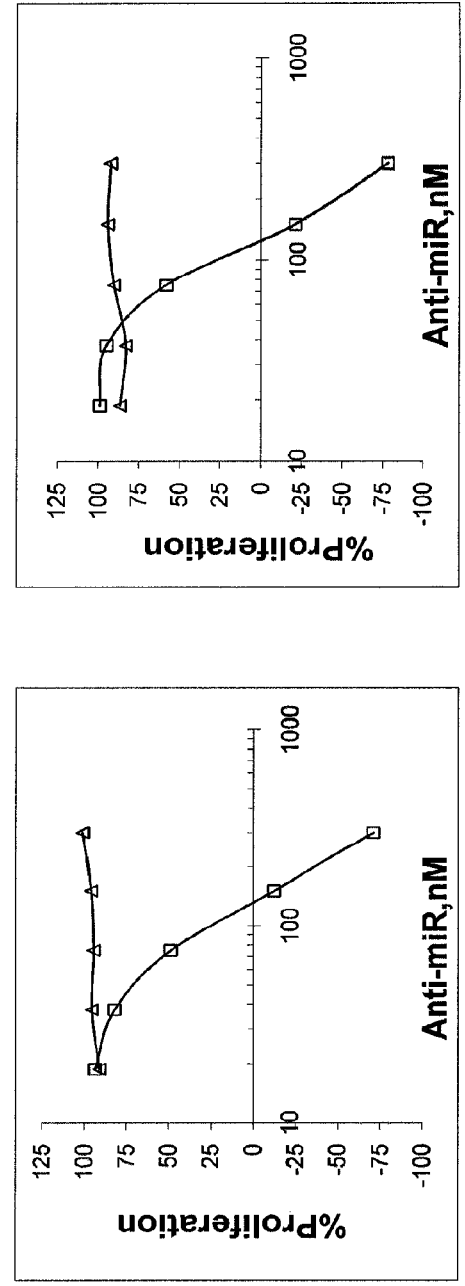
Figure 5A:
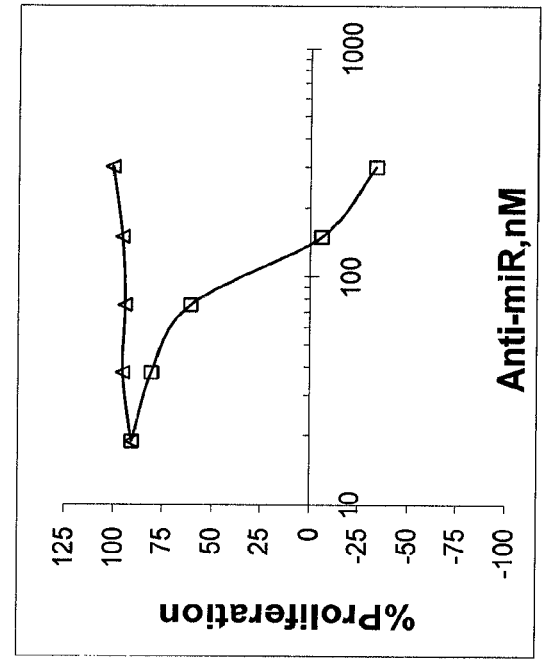
FIGS. 5A-5B demonstrate the effect of anti-miR (nM) (squares) on proliferate (percentage) of OVCAR-3 cells, 72 hours after transfection as compared to negative con anti-miR (triangles). 5A-anti-miR-22 (SEQ ID NO: 50), 5B-anti-miR-17 (SEQ ID NO: 44
Figure 5B:
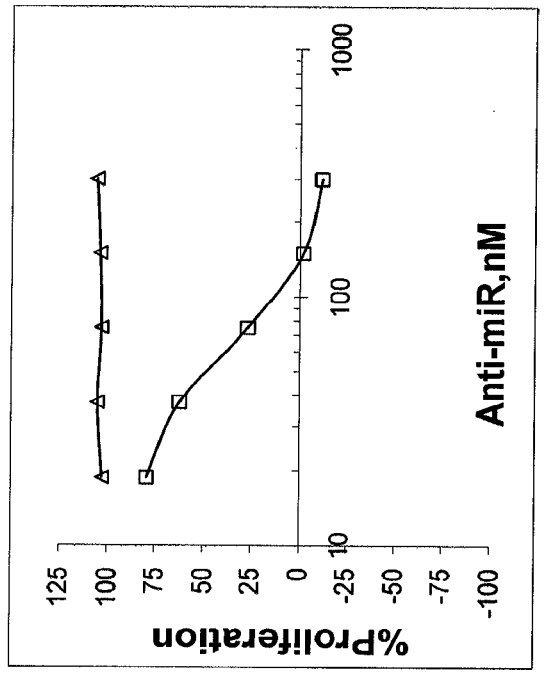

OVCAR-3 cells (ovarian adenocarcinoma), were used to study the effect of miR inhibition on proliferation of cells. Cells were transfected with increasing amounts of anti-miR in the range of 10-300 nM. Proliferation was assayed 72 hours after transfection. FIGS. 1-5 demonstrate the inhibition of proliferation for some of the upregulated and highly expressed miRs. Assay was repeated in SKOV-3 ovarian adenocarcinoma cells with similar trends. Table 3 shows the results of the concentration needed for 50% proliferation inhibition for the two cell lines. Negative control anti-miR was an oligonucleotide with similar chemical modifications, but an irrelevant sequence (Antisense for miR-122 harboring 6 missmatches).

TABLE 3

| Candidate | IC-50(nM) OVCAR-3 | IC-50(nM) SK-OV-3 |
|---|---|---|
| hsa-mir-100 | 60 | 60 |
| hsa-mir-103 | 32 | 38 |
| hsa-mir-125b | 48 | 80 |
| hsa-mir-17 | 82 | 280 |
| hsa-mir-18a | 100 | 300 |
| hsa-mir-191 | 40 | 30 |
| hsa-mir-20b | 45 | 90 |
| hsa-mir-21 | 70 | 50 |
| hsa-mir-210 | 65 | 58 |
| hsa-mir-22 | 50 | 55 |
| hsa-mir-221 | 85 | 65 |
| hsa-mir-23a | 82 | 60 |
| hsa-mir-24 | 38 | 68 |
| hsa-mir-25 | 85 | 65 |
| hsa-mir-26a | 28 | 58 |
| hsa-mir-27a | 68 | 150 |
| hsa-mir-31 | 75 | 100 |
| hsa-mir-99a | 42 | 60 |

Example 4

In Vivo Study

In order to demonstrate the efficacy of the anti-miR molecules of the invention, and the potential of those molecules in ovarian cancer therapy, an in vivo study is performed using a mouse model for peritoneal ovarian metastases.

30 female BALB/c nude mice are injected IP with $5 \times 10^6$ SKOV-3 cells in 200 ul PBS for tumor induction. 24 hours after tumor inoculation, anti-miR-oligonucleotides are injected IP every other day at a dose of 50 mg/Kg, for a period of two weeks into 15 animals. A second group of animals are injected with a control anti-miR with an irrelevant sequence.

The body weight and the survival of all animals are measured and vital parameters are monitored.

At termination of the study the following parameters are measured: tumors in the peritoneal cavity, number of tumor nodules, total tumor volume and weight, invasion into other organs and ascites volume.

Serum is sampled from the animals and the tumors are fresh frozen, and fixed in formalin for FFPE.

The following parameters are compared between the study and control groups: number of tumor nodules, total tumor volume, total tumor weight, ascites volume, CA-125 in serum, miR-concentration in the tumor using qRT-PCR, and in situ hybridization analysis of the specific miR in the tumor tissue.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method of inhibiting proliferation of ovarian cancer cells, the method consisting of introducing into the cells of a patient in need thereof a composition consisting of a compound which inhibits expression or activity of a nucleic acid sequence selected from the group consisting of SEQ ID NOs: 16 and 38, and a pharmaceutically acceptable carrier, wherein said compound inhibits proliferation of ovarian cancer cells.

2. The method of claim 1, wherein said compound comprises a modified oligonucleotide consisting of 15 to 30 linked nucleosides, wherein the modified oligonucleotide has a nucleobase sequence that is complementary to SEQ ID NO: 16 or 38.

3. The method of claim 2, wherein said modified oligonucleotide has a nucleobase sequence of SEQ ID NO: 56.

4. The method of claim 1, wherein the ovarian cancer cell is selected from the group consisting of serous and endometrioid ovarian cancer.

5. A method for treating ovarian cancer in a human subject in need thereof, said method consisting of administering to said subject a pharmaceutical composition consisting of a modified oligonucleotide and a pharmaceutically acceptable carrier, wherein the modified oligonucleotide consists of 15 to 30 linked nucleosides and has a nucleobase sequence that is complementary to a nucleobase sequence selected from the group consisting of SEQ ID NOs: 16 and 38.

6. The method of claim 5, wherein the modified oligonucleotide has a nucleobase sequence comprising at least 15 contiguous nucleobases of SEQ ID NO: 56.

7. The method of claim 5, wherein the ovarian cancer is selected from the group consisting of serous and endometrioid ovarian cancer.

8. The method of claim 4, wherein at least one internucleoside linkage of the modified oligonucleotide is a modified internucleoside linkage.

9. The method of claim 8, wherein said modified internucleoside linkage is a phosphorothioate internucleoside linkage.

10. The method of claim 2, wherein at least one nucleoside of the modified oligonucleotide comprises a modified sugar.

11. The method of claim 10, wherein the modified sugar is a 2'-O-methoxyethyl sugar.

12. The method of claim 5, wherein said composition is administered by any one of intravenous administration, subcutaneous administration, intratumoral administration, or chemoembolization.

13. The method of claim 5, wherein at least one internucleoside linkage of the modified oligonucleotide is a modified internucleoside linkage.

14. The method of claim 13, wherein said modified internucleoside linkage is a phosphorothioate internucleoside linkage.

15. The method of claim 5, wherein at least one nucleoside of the modified oligonucleotide comprises a modified sugar.

16. The method of claim 15, wherein the modified sugar is a 2'-O-methoxyethyl sugar.

\* \* \* \* \*

```
                            SEQUENCE LISTING

<160> NUMBER OF SEQ ID NOS: 58

<210> SEQ ID NO 1
<211> LENGTH: 22
<212> TYPE: RNA
<213> ORGANISM: Homo sapiens

<400> SEQUENCE: 1
aacccguaga uccgaacuug ug                                            22

<210> SEQ ID NO 2
<211> LENGTH: 23
<212> TYPE: RNA
<213> ORGANISM: Homo sapiens

<400> SEQUENCE: 2
agcagcauug uacagggcua uga                                           23

<210> SEQ ID NO 3
<211> LENGTH: 22
<212> TYPE: RNA
<213> ORGANISM: Homo sapiens

<400> SEQUENCE: 3
ucccugagac ccuaacuugu ga                                            22

<210> SEQ ID NO 4
<211> LENGTH: 23
<212> TYPE: RNA
<213> ORGANISM: Homo sapiens

<400> SEQUENCE: 4
caaagugcuu acagugcagg uag                                           23

<210> SEQ ID NO 5
<211> LENGTH: 23
<212> TYPE: RNA
<213> ORGANISM: Homo sapiens

<400> SEQUENCE: 5
uaaggugcau cuagugcaga uag                                           23

<210> SEQ ID NO 6
<211> LENGTH: 23
<212> TYPE: RNA
<213> ORGANISM: Homo sapiens

<400> SEQUENCE: 6
caacggaauc ccaaaagcag cug                                           23

<210> SEQ ID NO 7
<211> LENGTH: 23
<212> TYPE: RNA
<213> ORGANISM: Homo sapiens
```

```
<400> SEQUENCE: 7
caaagugcuc auagugcagg uag                                        23

<210> SEQ ID NO 8
<211> LENGTH: 22
<212> TYPE: RNA
<213> ORGANISM: Homo sapiens

<400> SEQUENCE: 8
uagcuuauca gacugauguu ga                                         22

<210> SEQ ID NO 9
<211> LENGTH: 22
<212> TYPE: RNA
<213> ORGANISM: Homo sapiens

<400> SEQUENCE: 9
cugugcgugu gacagcggcu ga                                         22

<210> SEQ ID NO 10
<211> LENGTH: 22
<212> TYPE: RNA
<213> ORGANISM: Homo sapiens

<400> SEQUENCE: 10
aagcugccag uugaagaacu gu                                         22

<210> SEQ ID NO 11
<211> LENGTH: 23
<212> TYPE: RNA
<213> ORGANISM: Homo sapiens

<400> SEQUENCE: 11
agcuacauug ucugcugggu uuc                                        23

<210> SEQ ID NO 12
<211> LENGTH: 21
<212> TYPE: RNA
<213> ORGANISM: Homo sapiens

<400> SEQUENCE: 12
aucacauugc cagggauuuc c                                          21

<210> SEQ ID NO 13
<211> LENGTH: 22
<212> TYPE: RNA
<213> ORGANISM: Homo sapiens

<400> SEQUENCE: 13
uggcucaguu cagcaggaac ag                                         22

<210> SEQ ID NO 14
<211> LENGTH: 22
<212> TYPE: RNA
<213> ORGANISM: Homo sapiens

<400> SEQUENCE: 14
cauugcacuu gucucggucu ga                                         22

<210> SEQ ID NO 15
<211> LENGTH: 22
<212> TYPE: RNA
<213> ORGANISM: Homo sapiens
```

-continued

<400> SEQUENCE: 15
uucaaguaau ccaggauagg cu            22

<210> SEQ ID NO 16
<211> LENGTH: 21
<212> TYPE: RNA
<213> ORGANISM: Homo sapiens

<400> SEQUENCE: 16
uucacagugg cuaaguuccg c             21

<210> SEQ ID NO 17
<211> LENGTH: 21
<212> TYPE: RNA
<213> ORGANISM: Homo sapiens

<400> SEQUENCE: 17
aggcaagaug cuggcauagc u             21

<210> SEQ ID NO 18
<211> LENGTH: 22
<212> TYPE: RNA
<213> ORGANISM: Homo sapiens

<400> SEQUENCE: 18
aacccguaga uccgaucuug ug            22

<210> SEQ ID NO 19
<211> LENGTH: 80
<212> TYPE: RNA
<213> ORGANISM: Homo sapiens

<400> SEQUENCE: 19
ccuguugcca caaacccgua gauccgaacu gugguauua guccgcacaa gcuuguaucu    60
auagguaugu gucuguuagg              80

<210> SEQ ID NO 20
<211> LENGTH: 78
<212> TYPE: RNA
<213> ORGANISM: Homo sapiens

<400> SEQUENCE: 20
uacugcccuc ggcuucuuua cagugcugcc uuguugcaua uggaucaagc agcauuguac    60
agggcuauga aggcauug                78

<210> SEQ ID NO 21
<211> LENGTH: 78
<212> TYPE: RNA
<213> ORGANISM: Homo sapiens

<400> SEQUENCE: 21
uugugcuuuc agcuucuuua cagugcugcc uuguagcauu caggucaagc agcauuguac    60
agggcuauga aagaacca                78

<210> SEQ ID NO 22
<211> LENGTH: 88
<212> TYPE: RNA
<213> ORGANISM: Homo sapiens

```
<400> SEQUENCE: 22
ugcgcuccuc ucagucccug agacccuaac uugugauguu uaccguuuaa auccacgggu    60
uaggcucuug ggagcugcga gucgugcu                                      88

<210> SEQ ID NO 23
<211> LENGTH: 89
<212> TYPE: RNA
<213> ORGANISM: Homo sapiens

<400> SEQUENCE: 23
accagacuuu uccuaguccc ugagacccua acuugugagg uauuuuagua acaucacaag    60
ucaggcucuu gggaccuagg cggagggga                                     89

<210> SEQ ID NO 24
<211> LENGTH: 84
<212> TYPE: RNA
<213> ORGANISM: Homo sapiens

<400> SEQUENCE: 24
gucagaauaa ugucaaagug cuuacagugc agguagugau augugcaucu acugcaguga    60
aggcacuugu agcauuaugg ugac                                          84

<210> SEQ ID NO 25
<211> LENGTH: 71
<212> TYPE: RNA
<213> ORGANISM: Homo sapiens

<400> SEQUENCE: 25
uguucuaagg ugcaucuagu gcagauagug aaguagauua gcaucuacug cccuaagugc    60
uccuucuggc a                                                        71

<210> SEQ ID NO 26
<211> LENGTH: 92
<212> TYPE: RNA
<213> ORGANISM: Homo sapiens

<400> SEQUENCE: 26
cggcuggaca gcgggcaacg gaaucccaaa agcagcuguu gucuccagag cauuccagcu    60
gcgcuuggau uucguccccu gcucuccugc cu                                 92

<210> SEQ ID NO 27
<211> LENGTH: 69
<212> TYPE: RNA
<213> ORGANISM: Homo sapiens

<400> SEQUENCE: 27
aguaccaaag ugcucauagu gcagguaguu uuggcaugac ucuacuguag uaugggcacu    60
uccaguacu                                                           69

<210> SEQ ID NO 28
<211> LENGTH: 72
<212> TYPE: RNA
<213> ORGANISM: Homo sapiens

<400> SEQUENCE: 28
ugucggguag cuuaucagac ugauguugac uguugaaucu cauggcaaca ccagucgaug    60
ggcugucuga ca                                                       72
```

-continued

```
<210> SEQ ID NO 29
<211> LENGTH: 110
<212> TYPE: RNA
<213> ORGANISM: Homo sapiens

<400> SEQUENCE: 29
acccggcagu gccuccaggc gcagggcagc cccugcccac cgcacacugc gcugcccag      60 acccacugug cgugugacag cggcugaucu gugccugggc agcgcgaccc              110

<210> SEQ ID NO 30
<211> LENGTH: 85
<212> TYPE: RNA
<213> ORGANISM: Homo sapiens

<400> SEQUENCE: 30
ggcugagccg caguaguucu ucaguggcaa gcuuuauguc cugacccagc uaaagcugcc      60
aguugaagaa cuguugcccu cugcc                                           85

<210> SEQ ID NO 31
<211> LENGTH: 110
<212> TYPE: RNA
<213> ORGANISM: Homo sapiens

<400> SEQUENCE: 31
ugaacaucca ggucuggggc augaaccugg cauacaaugu agauuucugu guucguuagg      60
caacagcuac auugucugcu ggguuucagg cuaccuggaa acauguucuc              110

<210> SEQ ID NO 32
<211> LENGTH: 73
<212> TYPE: RNA
<213> ORGANISM: Homo sapiens

<400> SEQUENCE: 32
ggccggcugg gguuccuggg gaugggauuu gcuuccuguc acaaaucaca uugccaggga      60
uuuccaaccg acc                                                        73

<210> SEQ ID NO 33
<211> LENGTH: 68
<212> TYPE: RNA
<213> ORGANISM: Homo sapiens

<400> SEQUENCE: 33
cuccggugcc uacugagcug auaucaguuc ucauuuuaca cacuggcuca guucagcagg      60
aacaggag                                                              68

<210> SEQ ID NO 34
<211> LENGTH: 73
<212> TYPE: RNA
<213> ORGANISM: Homo sapiens

<400> SEQUENCE: 34
cucugccucc cgugccuacu gagcugaaac acaguugguu uguguacacu ggcucaguuc      60
agcaggaaca ggg                                                        73

<210> SEQ ID NO 35
<211> LENGTH: 84
<212> TYPE: RNA
```

```
<400> SEQUENCE: 35
ggccaguguu gagaggcgga gacuugggca auugcuggac gcugcccugg gcauugcacu    60
ugucucgguc ugacagugcc ggcc                                          84

<210> SEQ ID NO 36
<211> LENGTH: 77
<212> TYPE: RNA
<213> ORGANISM: Homo sapiens

<400> SEQUENCE: 36
guggccucgu ucaaguaauc caggauaggc ugugcagguc ccaaugggcc uauucuuggu    60
uacuugcacg gggacgc                                                  77

<210> SEQ ID NO 37
<211> LENGTH: 84
<212> TYPE: RNA
<213> ORGANISM: Homo sapiens

<400> SEQUENCE: 37
ggcuguggcu ggauucaagu aauccaggau aggcuguuuc caucugugag gccuauucuu    60
gauuacuugu uucggaggc agcu                                           84

<210> SEQ ID NO 38
<211> LENGTH: 78
<212> TYPE: RNA
<213> ORGANISM: Homo sapiens

<400> SEQUENCE: 38
cugaggagca gggcuuagcu gcuugugagc aggguccaca ccaagucgug uucacagugg    60
cuaaguuccg cccccccag                                                78

<210> SEQ ID NO 39
<211> LENGTH: 71
<212> TYPE: RNA
<213> ORGANISM: Homo sapiens

<400> SEQUENCE: 39
ggagaggagg caagaugcug gcauagcugu ugaacuggga accugcuaug ccaacauauu    60
gccaucuuuc c                                                        71

<210> SEQ ID NO 40
<211> LENGTH: 81
<212> TYPE: RNA
<213> ORGANISM: Homo sapiens

<400> SEQUENCE: 40
cccauuggca uaaacccgua gauccgaucu uguggugaag uggaccgcac aagcucgcuu    60
cuaugggucu gugucagugu g                                             81

<210> SEQ ID NO 41
<211> LENGTH: 22
<212> TYPE: RNA
<213> ORGANISM: Artificial sequence
<220> FEATURE:
<223> OTHER INFORMATION: Synthetic

<400> SEQUENCE: 41
cacaaguucg gaucuacggg uu                                            22
```

<210> SEQ ID NO 42
<211> LENGTH: 23
<212> TYPE: RNA
<213> ORGANISM: Artificial sequence
<220> FEATURE:
<223> OTHER INFORMATION: Synthetic

<400> SEQUENCE: 42
ucauagcccu guacaaugcu gcu                                              23

<210> SEQ ID NO 43
<211> LENGTH: 22
<212> TYPE: RNA
<213> ORGANISM: Artificial sequence
<220> FEATURE:
<223> OTHER INFORMATION: Synthetic

<400> SEQUENCE: 43
ucacaaguua gggucucagg ga                                               22

<210> SEQ ID NO 44
<211> LENGTH: 23
<212> TYPE: RNA
<213> ORGANISM: Artificial sequence
<220> FEATURE:
<223> OTHER INFORMATION: Synthetic

<400> SEQUENCE: 44
cuaccugcac uguaagcacu uug                                              23

<210> SEQ ID NO 45
<211> LENGTH: 23
<212> TYPE: RNA
<213> ORGANISM: Artificial sequence
<220> FEATURE:
<223> OTHER INFORMATION: Synthetic

<400> SEQUENCE: 45
cuaucugcac uagaugcacc uua                                              23

<210> SEQ ID NO 46
<211> LENGTH: 23
<212> TYPE: RNA
<213> ORGANISM: Artificial sequence
<220> FEATURE:
<223> OTHER INFORMATION: Synthetic

<400> SEQUENCE: 46
cagcugcuuu ugggauuccg uug                                              23

<210> SEQ ID NO 47
<211> LENGTH: 23
<212> TYPE: RNA
<213> ORGANISM: Artificial sequence
<220> FEATURE:
<223> OTHER INFORMATION: Synthetic

<400> SEQUENCE: 47
cuaccugcac uaugagcacu uug                                              23

<210> SEQ ID NO 48
<211> LENGTH: 22
<212> TYPE: RNA
<213> ORGANISM: Artificial sequence
<220> FEATURE:
<223> OTHER INFORMATION: Synthetic

```
<400> SEQUENCE: 48
ucaacaucag ucugauaagc ua                                    22

<210> SEQ ID NO 49
<211> LENGTH: 22
<212> TYPE: RNA
<213> ORGANISM: Artificial sequence
<220> FEATURE:
<223> OTHER INFORMATION: Synthetic

<400> SEQUENCE: 49
ucagccgcug ucacacgcac ag                                    22

<210> SEQ ID NO 50
<211> LENGTH: 22
<212> TYPE: RNA
<213> ORGANISM: Artificial sequence
<220> FEATURE:
<223> OTHER INFORMATION: Synthetic

<400> SEQUENCE: 50
acaguucuuc aacuggcagc uu                                    22

<210> SEQ ID NO 51
<211> LENGTH: 23
<212> TYPE: RNA
<213> ORGANISM: Artificial sequence
<220> FEATURE:
<223> OTHER INFORMATION: Synthetic

<400> SEQUENCE: 51
gaaacccagc agacaaugua gcu                                   23

<210> SEQ ID NO 52
<211> LENGTH: 21
<212> TYPE: RNA
<213> ORGANISM: Artificial sequence
<220> FEATURE:
<223> OTHER INFORMATION: Synthetic

<400> SEQUENCE: 52
ggaaaucccu ggcaauguga u                                     21

<210> SEQ ID NO 53
<211> LENGTH: 22
<212> TYPE: RNA
<213> ORGANISM: Artificial sequence
<220> FEATURE:
<223> OTHER INFORMATION: Synthetic

<400> SEQUENCE: 53
cuguuccugc ugaacugagc ca                                    22

<210> SEQ ID NO 54
<211> LENGTH: 22
<212> TYPE: RNA
<213> ORGANISM: Artificial sequence
<220> FEATURE:
<223> OTHER INFORMATION: Synthetic

<400> SEQUENCE: 54
ucagaccgag acaagugcaa ug                                    22
```

```
<210> SEQ ID NO 55
<211> LENGTH: 22
<212> TYPE: RNA
<213> ORGANISM: Artificial sequence
<220> FEATURE:
<223> OTHER INFORMATION: Synthetic

<400> SEQUENCE: 55
agccuauccu ggauuacuug aa                                                  22

<210> SEQ ID NO 56
<211> LENGTH: 21
<212> TYPE: RNA
<213> ORGANISM: Artificial sequence
<220> FEATURE:
<223> OTHER INFORMATION: Synthetic

<400> SEQUENCE: 56
gcggaacuua gccacuguga a                                                   21

<210> SEQ ID NO 57
<211> LENGTH: 21
<212> TYPE: RNA
<213> ORGANISM: Artificial sequence
<220> FEATURE:
<223> OTHER INFORMATION: Synthetic

<400> SEQUENCE: 57
agcuaugcca gcaucuugcc u                                                   21

<210> SEQ ID NO 58
<211> LENGTH: 22
<212> TYPE: RNA
<213> ORGANISM: Artificial sequence
<220> FEATURE:
<223> OTHER INFORMATION: Synthetic

<400> SEQUENCE: 58
cacaagaucg gaucuacggg uu                                                  22
```